United States Patent
Bronkalla

(10) Patent No.: US 11,610,687 B2
(45) Date of Patent: Mar. 21, 2023

(54) AUTOMATED PEER REVIEW OF MEDICAL IMAGERY

(71) Applicant: Merative US L.P., Ann Arbor, MI (US)

(72) Inventor: Mark Bronkalla, Hartland, WI (US)

(73) Assignee: Merative US L.P., Ann Arbor, MI (US)

( * ) Notice: Subject to any disclaimer, the term of this patent is extended or adjusted under 35 U.S.C. 154(b) by 691 days.

(21) Appl. No.: 15/257,790

(22) Filed: Sep. 6, 2016

(65) Prior Publication Data

US 2018/0068066 A1   Mar. 8, 2018

(51) Int. Cl.
| | | |
|---|---|---|
| G16H 50/70 | (2018.01) | |
| G16H 50/20 | (2018.01) | |
| G16H 10/60 | (2018.01) | |
| G06F 16/00 | (2019.01) | |
| G16H 10/20 | (2018.01) | |
| G16H 30/40 | (2018.01) | |
| G16H 10/40 | (2018.01) | |
| G06F 40/30 | (2020.01) | |

(52) U.S. Cl.
CPC .............. *G16H 50/70* (2018.01); *G06F 16/00* (2019.01); *G06F 40/30* (2020.01); *G16H 10/20* (2018.01); *G16H 10/40* (2018.01); *G16H 10/60* (2018.01); *G16H 30/40* (2018.01); *G16H 50/20* (2018.01)

(58) Field of Classification Search
CPC ........ G16H 50/70; G16H 10/40; G16H 30/40; G16H 10/20; G16H 10/60; G16H 50/20; G06F 16/00; G06F 40/30
See application file for complete search history.

(56) References Cited

U.S. PATENT DOCUMENTS

| | | | | |
|---|---|---|---|---|
| 2003/0197616 | A1* | 10/2003 | Karamanian | G08B 21/10 340/601 |
| 2005/0020903 | A1* | 1/2005 | Krishnan | G16H 50/20 600/407 |
| 2005/0049497 | A1* | 3/2005 | Krishnan | G16H 50/20 600/437 |
| 2006/0149558 | A1* | 7/2006 | Kahn | G10L 15/063 704/278 |
| 2006/0274928 | A1* | 12/2006 | Collins | G16H 30/40 382/132 |

(Continued)

FOREIGN PATENT DOCUMENTS

| | | | | | |
|---|---|---|---|---|---|
| CN | | 1971567 A | * | 5/2007 | ............. G06T 19/00 |
| CN | | 103279632 A | * | 9/2013 | ........... A61B 5/7278 |

(Continued)

OTHER PUBLICATIONS

IQ.IP.com search (Year: 2020).*

(Continued)

*Primary Examiner* — Tan D Nguyen
(74) *Attorney, Agent, or Firm* — Foley Hoag LLP; Erik A. Huestis

(57) ABSTRACT

Automated peer review of medical imagery is provided. In some embodiments, at least one finding is determined for a present study. The present study has a subject anatomy. Based on the at least one finding and the subject anatomy, at least one prior study is selected. The at least one prior study has subject anatomy related to the subject anatomy of the present study and does not include the at least one finding. The at least one prior study is provided to a user for review with respect to the at least one finding.

13 Claims, 4 Drawing Sheets

(56) References Cited

U.S. PATENT DOCUMENTS

| | | | | |
|---|---|---|---|---|
| 2008/0126982 A1* | 5/2008 | Sadikali | ............... | G06F 19/321 |
| | | | | 715/810 |
| 2013/0129198 A1* | 5/2013 | Sherman | ............... | G06F 19/321 |
| | | | | 382/159 |
| 2014/0044331 A1* | 2/2014 | Fischer | ................. | G16H 30/20 |
| | | | | 382/131 |
| 2014/0074502 A1 | 3/2014 | Walker et al. | | |
| 2014/0142980 A1 | 5/2014 | Revell | | |
| 2014/0149407 A1* | 5/2014 | Qian | .................... | G06F 19/321 |
| | | | | 707/737 |
| 2015/0205917 A1* | 7/2015 | Mabotuwana | ........ | G06F 19/321 |
| | | | | 382/128 |
| 2016/0092633 A1* | 3/2016 | Revell | ................... | G06Q 50/24 |
| | | | | 705/2 |
| 2016/0314246 A1* | 10/2016 | Roberge | ................ | G16H 15/00 |
| 2017/0177795 A1* | 6/2017 | Mabotuwana | ....... | A61B 6/5217 |
| 2018/0060512 A1* | 3/2018 | Sorenson | ................ | G06K 9/46 |

FOREIGN PATENT DOCUMENTS

| | | | | | |
|---|---|---|---|---|---|
| CN | 103999087 A | * | 8/2014 | ........... | G06F 16/583 |
| EP | 1884894 A1 | * | 2/2008 | | |
| WO | WO-03077552 A1 | * | 9/2003 | ............... | G06T 7/20 |
| WO | WO2006/019547 A1 | * | 2/2006 | | |
| WO | WO2008/024083 A3 | * | 7/2008 | | |

OTHER PUBLICATIONS

Constantinescu, Liviu, A patient-centric distribution architecture for Medical Image Sharing, Health Information Science and Systems, 1, 3, (Year: 2013).*

Abder-Rahman A., "A systematic review of automated melanoma detection in dermatoscopic images and its ground truth data", Feb. 28, 2012, Proceedings vol. 8318, Medical Imaging 2012, paper. (Year: 2012).*

Meindert Niemeijer, "Retinopathy Online Challenge Automatic Detection of . . . Fundus Photographs", Jan. 2010, IEEE Transactions on Medical Imaging, vol. 29, No. 1, pp. 185-195. (Year: 2010).*

Michael Bruno, "Understanding and Confronting Our Mistakes: The Epidemiology of Error in Radiology and Strategies for Error Reduction", 2015, RSAN, pp. 1668-1676. (Year: 2015).*

* cited by examiner

AUTOMATED PEER REVIEW OF MEDICAL IMAGERY

BACKGROUND

Embodiments of the present invention relate to analyzing medical images, and more specifically, to automated peer review of medical imagery.

BRIEF SUMMARY

According to embodiments of the present disclosure, methods of and computer program products for analyzing medical images are provided. At least one finding is determined for a present study. The present study has a subject anatomy. Based on the at least one finding and the subject anatomy, at least one prior study is selected. The at least one prior study has subject anatomy related to the subject anatomy of the present study and does not include the at least one finding. The at least one prior study is provided to a user for review with respect to the at least one finding.

According to additional embodiments of the present disclosure, methods of and computer program products for analyzing medical images are provided. At least one finding is determined for a present study. The present study has a subject anatomy. Based on the at least one finding and the subject anatomy, at least one prior study is selected. The at least one prior study has subject anatomy related to the subject anatomy of the present study. Whether the at least one finding is associated with the at least one prior study is determined.

DETAILED DESCRIPTION

Figure 1:
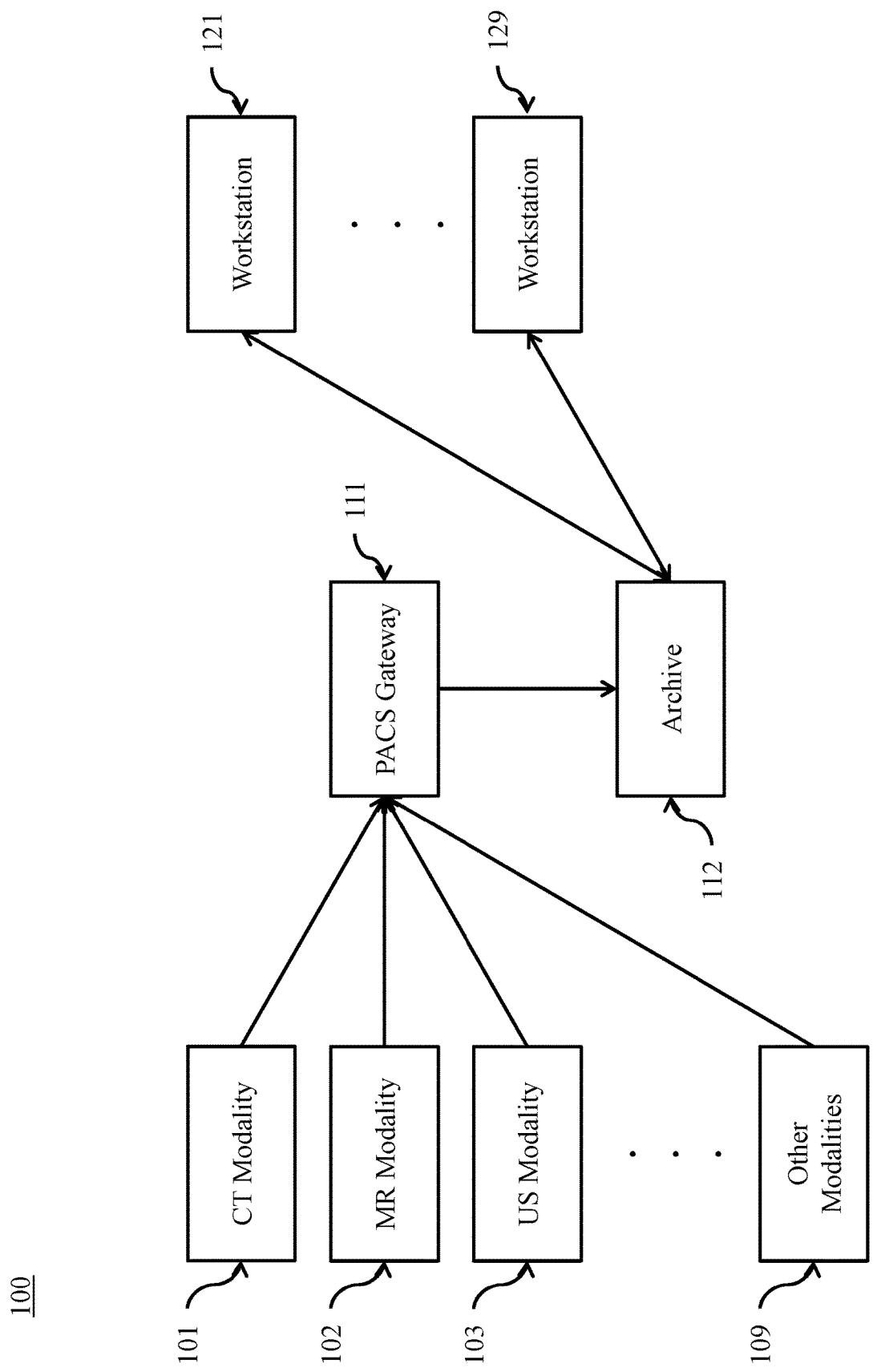
FIG. 1 depicts an exemplary Picture Archiving and Communication System.

A Picture Archiving and Communication System (PACS) is a medical imaging system that provides storage and access to images from multiple modalities. In many healthcare environments, electronic images and reports are transmitted digitally via PACS, thus eliminating the need to manually file, retrieve, or transport film jackets. A standard format for PACS image storage and transfer is DICOM (Digital Imaging and Communications in Medicine). Non-image data, such as scanned documents, may be incorporated using various standard formats such as PDF (Portable Document Format) encapsulated in DICOM.

The standard peer review process is a lengthy and complicated one that involves many legacy processes. These processes often miss relevant data that would assist in a comprehensive review. Accordingly, there is a need for a reliable, automated process for peer review that integrates into a PACS.

In various embodiments of the present disclosure, an analysis system such as Watson is used for automated PACS-based peer review. In some embodiments, prior comparison review suggestions are provided. In such embodiments, indications for a current study are used to check past impressions of the same body part and flag priors for review. In some embodiments, automatic comparison of current and prior reports for the same body part is performed. In such embodiments, differing impressions are flagged and suggested for follow up. In some embodiments, prior comparisons of related body part are suggested for review. For example, for a current lung screening CT, a prior cardiac CT study, chest CT, or chest X-rays from various dates may be flagged. Computer-Aided Diagnosis/Detection (CAD) may be run on these prior studies before the reading of the current lung CT to provide additional context for the present reading. In some embodiments, negative and unmentioned subsequent impressions may be flagged for follow-up. In some embodiments, prior report indications may be flagged for follow-up tracking.

In various embodiments of the present disclosure, an analysis system such as Watson is used for assisting in assigned peer review, in particular for current study sampling and assignment. In some embodiments, peer review and assignment is risk stratified. In particular, assignment is based on study types rather than just modality to provide double over-read of high risk or low incidence studies. In some embodiments, automated blinding is provided.

In various embodiments of the present disclosure, an analysis system such as Watson is used for semi-automated peer review based on non-radiology sources. In some embodiments, biopsy are radiology report comparisons are provided. In particular, the hit rate/accuracy of readers is determined based on false true positives. In some embodiments, MR arthroscopy reading results and later surgical intervention results are assessed for accuracy. In particular, whether the surgeon actually found what appeared to be a problem in the MR exam or found things that were missed in the MR exam are determined.

Referring to FIG. 1, an exemplary PACS 100 consists of four major components. Various imaging modalities 101 . . . 109 such as computed tomography (CT) 101, magnetic resonance imaging (MRI) 102, or ultrasound (US) 103 provide imagery to the system. In some implementations, imagery is transmitted to a PACS Gateway 111, before being stored in archive 112. Archive 112 provides for the storage and retrieval of images and reports. Workstations 121 . . . 129 provide for interpreting and reviewing images in archive 112. In some embodiments, a secured network is used for the transmission of patient information between the components of the system. In some embodiments, workstations 121 . . . 129 may be web-based viewers. PACS delivers timely and efficient access to images, interpretations, and related data, eliminating the drawbacks of traditional film-based image retrieval, distribution, and display.

A PACS may handle images from various medical imaging instruments, such as X-ray plain film (PF), ultrasound (US), magnetic resonance (MR), Nuclear Medicine imaging, positron emission tomography (PET), computed tomography (CT), endoscopy (ES), mammograms (MG), digital radiography (DR), computed radiography (CR), Histopathology, or ophthalmology. However, a PACS is not limited to a predetermined list of images, and supports clinical areas beyond conventional sources of imaging such as radiology, cardiology, oncology, or gastroenterology.

Different users may have a different view into the overall PACS system. For example, while a radiologist may typically access a viewing station, a technologist may typically access a QA workstation.

In some implementations, the PACS Gateway 111 comprises a quality assurance (QA) workstation. The QA workstation provides a checkpoint to make sure patient demographics are correct as well as other important attributes of a study. If the study information is correct the images are passed to the archive 112 for storage. The central storage device, archive 112, stores images and in some implementations, reports, measurements and other information that resides with the images.

Once images are stored to archive 112, they may be accessed from reading workstations 121 . . . 129. The reading workstation is where a radiologist reviews the patient's study and formulates their diagnosis. In some implementations, a reporting package is tied to the reading workstation to assist the radiologist with dictating a final report. A variety of reporting systems may be integrated with the PACS, including those that rely upon traditional dictation. In some implementations, CD or DVD authoring software is included in workstations 121 . . . 129 to burn patient studies for distribution to patients or referring physicians.

In some implementations, a PACS includes web-based interfaces for workstations 121 . . . 129. Such web interfaces may be accessed via the internet or a Wide Area Network (WAN). In some implementations, connection security is provided by a VPN (Virtual Private Network) or SSL (Secure Sockets Layer). The clients side software may comprise ActiveX, JavaScript, or a Java Applet. PACS clients may also be full applications which utilize the full resources of the computer they are executing on outside of the web environment.

Communication within PACS is generally provided via Digital Imaging and Communications in Medicine (DICOM). DICOM provides a standard for handling, storing, printing, and transmitting information in medical imaging. It includes a file format definition and a network communications protocol. The communication protocol is an application protocol that uses TCP/IP to communicate between systems. DICOM files can be exchanged between two entities that are capable of receiving image and patient data in DICOM format.

DICOM groups information into data sets. For example, a file containing a particular image, generally contains a patient ID within the file, so that the image can never be separated from this information by mistake. A DICOM data object consists of a number of attributes, including items such as name and patient ID, as well as a special attribute containing the image pixel data. Thus, the main object has no header as such, but instead comprises a list of attributes, including the pixel data. A DICOM object containing pixel data may correspond to a single image, or may contain multiple frames, allowing storage of cine loops or other multi-frame data. DICOM supports three- or four-dimensional data encapsulated in a single DICOM object. Pixel data may be compressed using a variety of standards, including JPEG, Lossless JPEG, JPEG 2000, and Run-length encoding (RLE). LZW (zip) compression may be used for the whole data set or just the pixel data.

Figure 2:
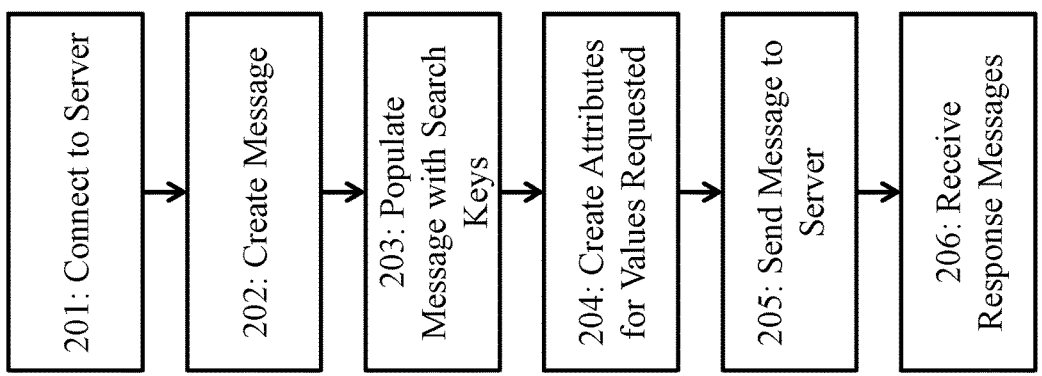
FIG. 2 illustrates an exemplary clinical image search and retrieval method.

Referring to FIG. 2, an exemplary PACS image search and retrieval method 200 is depicted. Communication with a PACS server, such as archive 112, is done through DICOM messages that that contain attributes tailored to each request. At 201, a client, such as workstation 121, establishes a network connection to a PACS server. At 202, the client prepares a DICOM message, which may be a C-FIND, C-MOVE, C-GET, or C-STORE request. At 203, the client fills in the DICOM message with the keys that should be matched. For example, to search by patient ID, a patient ID attribute is included. At 204, the client creates empty attributes for all the values that are being requested from the server. For example, if the client is requesting an image ID suitable for future retrieval of an image, it include an empty attribute for an image ID in the message. At 205, the client send the message to the server. At 206, the server sends back to the client a list of one or more response messages, each of which includes a list of DICOM attributes, populated with values for each match.

An electronic health record (EHR), or electronic medical record (EMR), may refer to the systematized collection of patient and population electronically-stored health information in a digital format. These records can be shared across different health care settings and may extend beyond the information available in a PACS discussed above. Records may be shared through network-connected, enterprise-wide information systems or other information networks and exchanges. EHRs may include a range of data, including demographics, medical history, medication and allergies, immunization status, laboratory test results, radiology images, vital signs, personal statistics like age and weight, and billing information.

EHR systems may be designed to store data and capture the state of a patient across time. In this way, the need to track down a patient's previous paper medical records is eliminated. In addition, an EHR system may assist in ensuring that data is accurate and legible. It may reduce risk of data replication as the data is centralized. Due to the digital information being searchable, EMRs may be more effective when extracting medical data for the examination of possible trends and long term changes in a patient. Population-based studies of medical records may also be facilitated by the widespread adoption of EHRs and EMRs.

Health Level-7 or HL7 refers to a set of international standards for transfer of clinical and administrative data between software applications used by various healthcare providers. These standards focus on the application layer, which is layer 7 in the OSI model. Hospitals and other healthcare provider organizations may have many different computer systems used for everything from billing records to patient tracking. Ideally, all of these systems may communicate with each other when they receive new information or when they wish to retrieve information, but adoption of such approaches is not widespread. These data standards are meant to allow healthcare organizations to easily share clinical information. This ability to exchange information may help to minimize variability in medical care and the tendency for medical care to be geographically isolated.

In various systems, connections between a PACS, Electronic Medical Record (EMR), Hospital Information System (HIS), Radiology Information System (RIS), or report repository are provided. In this way, records and reports form the EMR may be ingested for analysis. For example, in addition to ingesting and storing HL7 orders and results messages, ADT messages may be used, or an EMR, RIS, or report repository may be queried directly via product specific mechanisms. Such mechanisms include Fast Health Interoperability Resources (FHIR) for relevant clinical information. Clinical data may also be obtained via receipt of various HL7 CDA documents such as a Continuity of Care Document (CCD). Various additional proprietary or site-customized query methods may also be employed in addition to the standard methods.

Figure 3:
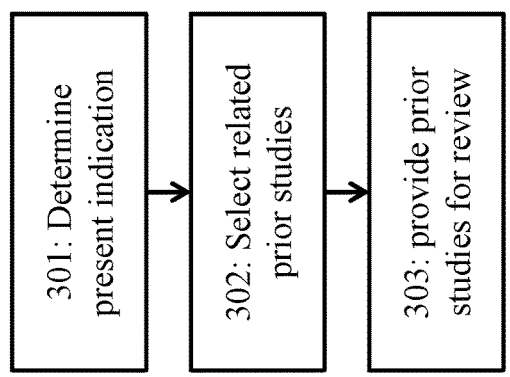
FIG. 3 illustrates an exemplary method for analyzing medical images according to embodiments of the present disclosure.

Referring now to FIG. 3, a method 300 for analyzing medical images is illustrated. At 301, at least one finding is determined for a present study. The present study has a subject anatomy. At 302, based on the at least one finding and the subject anatomy, at least one prior study is selected. The at least one prior study has subject anatomy related to the subject anatomy of the present study and does not include the at least one finding. At 303, the at least one prior study is provided to a user for review with respect to the at least one finding.

In some embodiments, the at least one finding is determined from a pathology report or a surgical note. In some such embodiments, the at least one finding is determined from the pathology report or the surgical note by natural language processing. In some embodiments, the at least one finding is determined from medical imagery. In some such embodiments, the at least one finding is determined by applying computer-aided diagnosis to the medical imagery. In some such embodiments, the at least one finding is determined from image annotation. In some embodiments, the at least one prior study is selected such that it can support or refute the at least one finding upon review. In some embodiments, the at least one prior study are providing to the user for review as a time series. In some embodiments, the at least one prior study has an original reviewer, and the user for review is selected to be other than the original reviewer.

In various embodiments, additional services are provided including automatically aggregating results across many facilities, practices and readers and thereby providing accuracy benchmarks for specific study types. This allows development of compelling practice accuracy metrics not only for internal performance review and improvement, utilization review and management, but also as a selling tool for the practices to use when bidding for radiology reading contracts. Other distribution channel for the results would be to insurance companies, and even consumers.

In various embodiments, over-reading of studies for accuracy is provided. In such embodiments, image data is used with current patient history information to make a determination on accuracy. This may be presented in real time during the reporting process rather than being done retrospectively to make the information more actionable and useful to the patient.

In various embodiments, cross-correlation of the imaging studies with other data is performed to confirm or deny the findings raised in the report. This may be based on a mixture of natural language processing and image feature extraction. For example, a shoulder MM that was read as being indicative of a rotator cuff tear, after which a surgeon operated, repaired and confirmed the finding provides a confirmation. An orthopedic surgeon doing an arthroscopy procedure and not finding a tear, but instead finding something else such as arthritis provides a denial of the report findings. In this case, there would be a mixture of NLP from the operative or surgeons notes form the EMR and arthroscopic photos taken during the procedure. Systems prior to the present disclosure lack systematic correlation of surgical findings with the precursor imaging study findings for use in quality metrics, training of the reader and technologists, or for creation of teaching files.

In various embodiments, cross-correlation of the imaging studies and pathology results is provided. An example cases is of a screening study (e.g., mammography) that is followed by a diagnostic study (e.g., breast biopsy) where the tissue is sent to pathology. Systems according to the present disclosure trigger on the pathology report creation and search for the predecessor imaging studies. The diagnostic accuracy is then computed and reported (positive or negative).

In various embodiments, cross-correlation of imaging studies with surgical results and pathology reports is provided. Use cases include the findings of what is identified as a cancerous lesion on an imaging study (CT, MR, PETG, NM). A radiologist report may state the suspected size/extent, location, number of lesions, etc. When surgically removed and the specimens are reviewed by the pathologist (typically during the surgical procedure), there is not only additional information about whether the lesion is cancerous or not, but of possible origin (native to the organ or a likely metastasis), the actual extent (is it much larger or smaller than the imaging study indicated), etc.

In various embodiments, cross-correlation of radiology imaging studies and endoscopy results is provided. In such embodiments, images are correlated to images and images are correlated to report NLP extraction. For example, a virtual colonoscopy was performed (CT colonography) and there were indications of a polyp that was deemed to need excision. In this example, this was then followed by a colonoscopy and removal. The results from the endoscopy study, image, surgical notes, and if excised the pathology report, are all cross-correlated against the CT study for accuracy. Additionally, there may be a differing number of polyps or lesions discovered during the colonoscopy.

According to various embodiments, when reading a current study for a patient the past study records for that patient are processed (both reports NLP and image cognition) and compared to the current study both as prior positive findings to reconfirm and as incidental findings (e.g., a mass was seen but dismissed as benign).

According to various embodiments, follow-up tracking for recommendations of additional exams is provided for the primary reason for the exam (e.g., breast US for follow-up to a suspicious mammogram) or for incidental findings (e.g., nodule seen on chest x-ray when looking for pneumonia or on a cardiac CT study. This allows a looks at the performance of the institution in follow-ups. Since in many cases the follow up study may be performed at a different (competitive) facility this is not tracked. However, overall insurance billing for that patient data may also be analyzed, through which the follow-up exam can definitively be tracked. Accordingly, systems of the present disclosure lead to better metrics on follow-up as well as increased revenue opportunities to contact the patient to come in for the follow-up exam.

In most facilities these are poorly correlated findings, and such facilities lack systematic and automated means of discovering and tracking the results and their accuracy. Additionally, follow-up may performed at an entirely different and unrelated facility (e.g., a study is performed at a private practice imaging center and the surgery is performed at a hospital). These entities may be completely unrelated and physicians at one facility may not have privileges at the other. In some embodiments, automated peer review and follow-up tracking is deidentified and aggregated to accommodate this case.

According to various embodiments, flagging of difficult to read, high error and high risk/low incidence studies for over reads is provided. In some embodiments, this is based on NLP of the reports.

When performing systematic peer review, there is a portion of the studies that are over-read for accuracy by a different reader (typically 2-5% by specialty). However, there are biases that can interfere and it is desirable to be able to automatically blind/anonymize the study (patient demographics), referring/ordering physician, technologist or operator that obtained the images, reading physician and other data. However, performing this process manually is time-consuming and error-prone and in the majority of sites, blinding is not done. With NLP, the text of the report can be scanned and blinded or have substitutions added. The images could be automatically anonymized. This may be applied to not only the study that was sent for peer review but also for the prior/comparison exams for that same patient as these may either have been used in the original reading of the study or should have been used in the reading of the original study and were omitted as comparisons for a variety of reasons.

Figure 4:
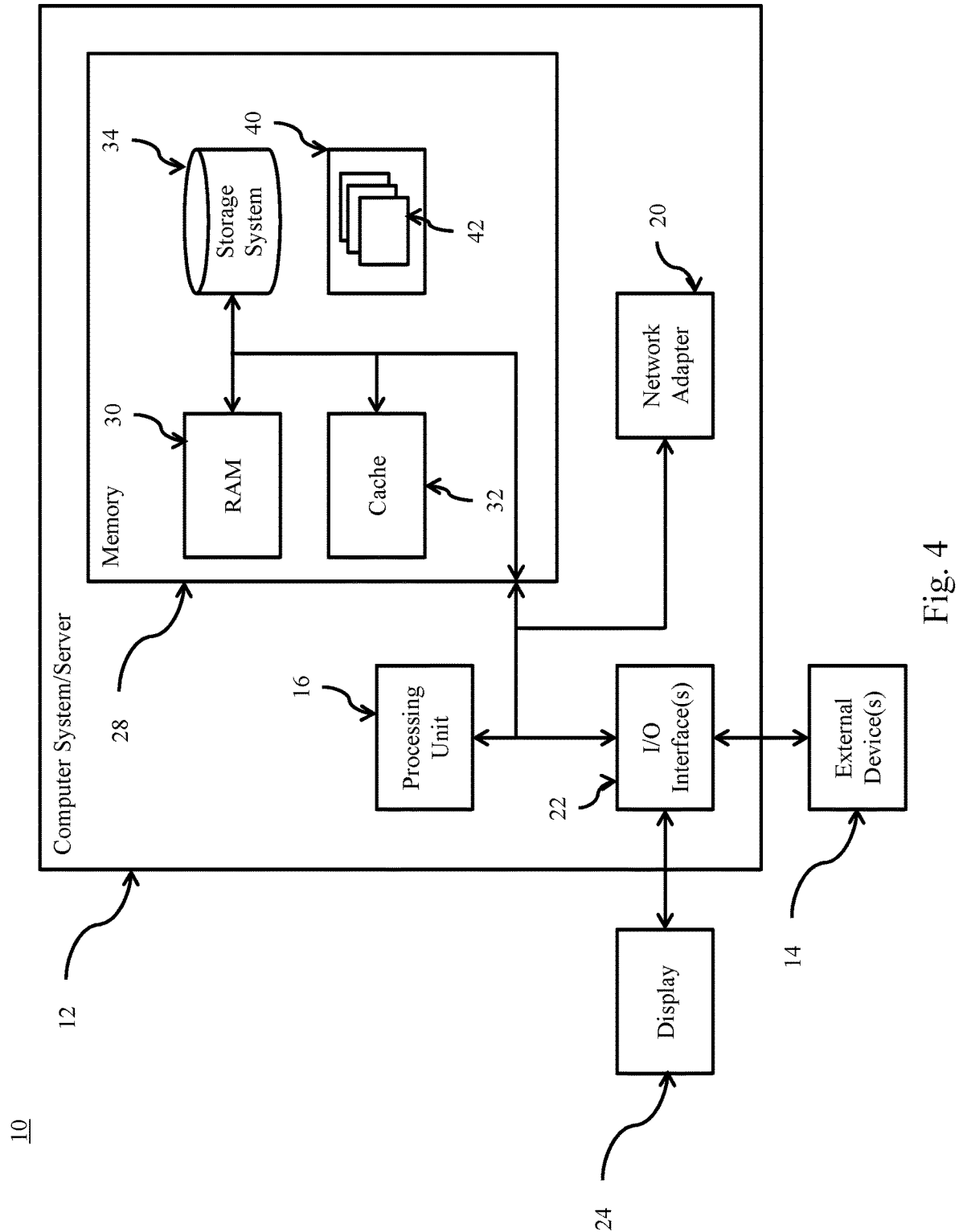
FIG. 4 depicts a computing node according to an embodiment of the present invention.

Referring now to FIG. 4, a schematic of an example of a computing node is shown. Computing node 10 is only one example of a suitable computing node and is not intended to suggest any limitation as to the scope of use or functionality of embodiments of the invention described herein. Regardless, computing node 10 is capable of being implemented and/or performing any of the functionality set forth hereinabove.

In computing node 10 there is a computer system/server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 4, computer system/server 12 in computing node 10 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the invention.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, external disk drive arrays, RAID systems, tape drives, and data archival storage systems, etc.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method comprising:
    determining, at a remote server, at least one finding for a present study by applying computer-aided diagnosis comprising at least one of: image cognition to at least one image in the present study, natural language processing of at least one note in the present study, or extraction of image annotation in the present study, the present study comprising a pathology report or surgical report, the present study having a subject anatomy;
    determining, at the remote server, based on the at least one finding and the subject anatomy of the present study, at least one prior study that does not include the at least one finding of the present study from a plurality of prior studies by applying natural language processing to text from each of the plurality of prior studies, each prior study comprising a prior radiology report, each prior radiology report including the subject anatomy and having occurred before the present study;

determining, at the remote server, at least one additional finding from the at least one prior study by applying computer-aided diagnosis comprising image cognition to each prior radiology report in the at least one prior study;

determining, at the remote server, whether the at least one finding of the present study is associated with the at least one additional finding of the at least one prior study by cross-correlating the at least one finding of the present study with the at least one additional finding of the at least one prior study;

when the at least one finding of the present study is associated with the at least one additional finding, flagging the at least one prior study for review; and loading the flagged at least one prior study into a Picture Archiving and Communication System (PACS) workstation for review.

2. The method of claim 1, further comprising:
computing an accuracy score based on whether the at least one finding is associated with the at least one previous finding of the at least one prior study.

3. The method of claim 1, further comprising:
providing, over a network, the at least one prior study to a user for review with respect to the at least one finding.

4. The method of claim 1, wherein the at least one prior study is selected such that it can support or refute the at least one finding upon review.

5. The method of claim 1, wherein the at least one prior study are providing to the user for review as a time series.

6. The method of claim 1, wherein the at least one finding is determined from the pathology report or the surgical note by natural language processing.

7. The method of claim 1, wherein the at least one finding is determined from image annotation.

8. The method of claim 1, wherein the at least one prior study having an original reviewer, and wherein the user for review is selected to be other than the original reviewer.

9. A computer program product for analyzing medical images, the computer program product comprising a computer readable storage medium having program instructions embodied therewith, the program instructions executable by a processor to cause the processor to perform a method comprising:

determining, at a remote server, at least one finding for a present study by applying computer-aided diagnosis comprising at least one of: image cognition to at least one image in the present study, natural language processing of at least one note in the present study, or extraction of image annotation in the present study, the present study comprising a pathology report or surgical report, the present study having a subject anatomy;

determining, at the remote server, based on the at least one finding and the subject anatomy of the present study, at least one prior study that does not include the at least one finding of the present study from a plurality of prior studies by applying natural language processing to text from each of the plurality of prior studies, each prior study comprising a prior radiology report, each prior radiology report including the subject anatomy and having occurred before the present study;

determining, at the remote server, at least one additional finding from the at least one prior study by applying computer-aided diagnosis comprising image cognition to each prior radiology report in the at least one prior study;

determining, at the remote server, whether the at least one finding of the present study is associated with the at least one additional finding of the at least one prior study by cross-correlating the at least one finding of the present study with the at least one additional finding of the at least one prior study;

when the at least one finding of the present study associated with the at least one additional finding, flagging the at least one prior study for review; and loading the flagged at least one prior study into a Picture Archiving and Communication System (PACS) workstation for review.

10. The computer program product of claim 9, the method further comprising:
computing an accuracy score based on whether the at least one finding is associated with the at least one previous finding of the at least one prior study.

11. The computer program product of claim 9, the method further comprising:
providing, over a network, the at least one prior study to a user for review with respect to the at least one finding.

12. The computer program product of claim 9, wherein the at least one prior study is selected such that it can support or refute the at least one finding upon review.

13. The computer program product of claim 9, wherein the at least one prior study are providing to the user for review as a time series.

* * * * *